United States Patent [19]

Sadhir et al.

[11] Patent Number: 5,306,643
[45] Date of Patent: Apr. 26, 1994

[54] METHOD FOR DETECTING LOW LEVELS OF ALKYLBENZENE OR MINERAL OIL IN POLYOL ESTER LUBRICANTS IN THE COMPRESSORS

[75] Inventors: Rajender K. Sadhir, Plum Boro, Westmoreland County, Pa.; Jeffrey B. Berge, Edina, Minn.

[73] Assignee: Westinghouse Electric Corp., Pittsburgh, Pa.

[21] Appl. No.: 114,404

[22] Filed: Sep. 1, 1993

[51] Int. Cl.$^5$ .................. G01N 33/00; G01N 31/00
[52] U.S. Cl. .................. 436/140; 436/39; 436/40; 436/60; 436/139
[58] Field of Search ............. 436/39, 40, 60, 139, 436/140

[56] References Cited

U.S. PATENT DOCUMENTS

| | | | |
|---|---|---|---|
| 174,506 | 3/1876 | Everest | 436/60 X |
| 4,203,725 | 5/1980 | Snowden, Jr. et al. | 436/60 |
| 4,686,192 | 8/1987 | Fisher | 436/60 |
| 4,873,056 | 10/1989 | Fisher | 436/60 X |

OTHER PUBLICATIONS

*Merck Index*, 11th Edition, Merck & Co., Inc. (1989), entry 5868.

*Primary Examiner*—James C. Housel
*Assistant Examiner*—Milton I. Cano
*Attorney, Agent, or Firm*—M. J. Moran

[57] ABSTRACT

A method for detecting low level of alkylbenzene or mineral oil impurity in polyol ester lubricants for compressors. This method comprises mixing a mixture of alcohol and water with a sample of the lubricant and then observe the presence or absence of turbidity.

6 Claims, No Drawings

METHOD FOR DETECTING LOW LEVELS OF ALKYLBENZENE OR MINERAL OIL IN POLYOL ESTER LUBRICANTS IN THE COMPRESSORS

BACKGROUND OF THE INVENTION

The present invention relates to a novel method of detecting low levels of impurities in lubricants for compressors. More particularly, this invention relates to a novel but simple method for detecting low levels of alklybenzene or mineral oil which may be present as an impurity in polyol ester (POE) lubricants in compressors.

Lubricants are generally added in refrigeration units in order to protect and prolong the life of the frictionally engaged machine components from wear. One class of lubricants comprises, for example, mineral oils. They are produced by known techniques such as by distillation of crude and subsequent refining of petroleum. Depending on the origin of the raw material petroleum, mineral oils produced may be designated paraffin-or naphthenic-base lubricating oil. Paraffin-base lubricating oils comprise paraffinic molecules while naphthenic-base oil comprise napthenic or cycloparaffinic molecules. These oils generally do not contain additives. To improve wear resistance additives such as phosphate esters have been suggested.

Another class of lubricants comprises alkylbenzenes. They have the general formula as shown in FIG. 1.

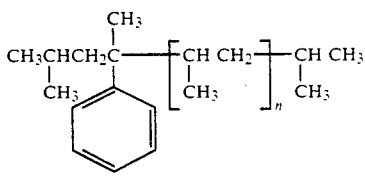

Figure 1 in which n is a positive integer.

The alkylbenzenes are produced by the known Friedel Crafts synthesis such as by alkylation of benzene with alkylchlorides or olefins. Lubricants serve a very important function in refrigeration units. Low levels of lubricants or impurities therein could cause premature fatigue resulting in failure of engaged machine components. A satisfactory lubricant should exhibit good low-temperature characteristics and thermal stability.

Commercial manufactures such as Thermo King has a large number of refrigeration units in the field which are operating with R-12 which is a fluoro carbon refrigerant and alkylbenzene or mineral oil as lubricants in the refrigeration systems. With the legislative changes which prohibit the use of high Ozone Depletion Potential (ODP) and high Global Warming Potential (GWP) refrigerants, R-I2 refrigerant will be banned in the near future. The retrofit of these compressors will require a change from chlorinated fluorinated hydrocarbon (CFCs) to fluorinated hydrocarbon (HFCs), such as R-134a. Due to incompatibility of R-134a which is tetrafluoro ethane, with the presently used lubricants (alkylbenzene and mineral oil), new polyol ester (POE) lubricants have to be used. The retrofit procedure recommended by the refrigerant and lubricant manufacturers and our own studies suggest at least three separate lubricant changes in the compressor in order to remove the existing lubricant to an acceptable level.

It has been documented in some studies and further confirmed by miscibility studies that even low concentrations of alkylbenzene or mineral oil in polyol ester can alter the low temperature miscibility drastically. Poor miscibility will affect the performance of the lubricant at low temperature. Table 1 shows the adverse effects of low levels of mineral oil which is present as an impurity in the Castrol SW-32 a polyol ester lubricant.

TABLE 1

| Effect of Mineral Oil Impurity in POE Lubricant on Miscibility Miscibility of 90% R-134a and 10 SW-32 | |
|---|---|
| Mineral Oil Impurity Level (% of Oil) | Lowest Temperature Miscibility °C. |
| 0 | < −50 |
| 1 | −35 |
| 3 | 0 |
| 5 | +18 |

These results suggest that it is important to reduce the mineral oil/alkylbenzene concentration in POE to a minimum during retrofitting.

At present there is no practical method to detect low concentrations of impurities in the form of alkylbenzene/mineral oil in POE, especially where the refrigeration units had been installed. Typical procedures recommended to refrigeration engineers for retrofitting requires three changes of the POE lubricant, which reduces the concentration of alkylbenzene or mineral oil to less than 3%. The method used for testing the presence of the impurity involves withdrawing a sample and then determining the level of the said impurity by infrared (IR) spectroscopy. When an operator is carrying out this procedure in the field, it is obviously inconvenient to service the test and requires an IR instrument.

SUMMARY OF THE INVENTION

According to the present invention, there is provided a simple yet accurate method for the rapid identification of the presence of low level of alkylbenzene or mineral oil which may be present in polyol ester lubricants. The POE lubricants are being used to replace existing lubricants (i.e. alkylbenzene or mineral oil) in existing refrigeration units.

Briefly, the method according to the present invention comprises adding a sufficient amount of an alcohol-water mixture to a sample of the lubricant. If the sample contains no impurities, i.e substantially pure POE, the solution remains clear. On the other hand, if there is alkylbenzene or mineral oil present in the sample the solution becomes opaque thereby affording the field engineers a quick determination of impurity in the sample. A typical alcohol-water mixture is a methanol-water mixture.

DETAILED DESCRIPTION OF THE INVENTION

In accordance with the present invention provided a simple yet accurate method for detecting low levels of alklybenzene or mineral oil which may be present as impurities in lubricants such as polyol ester (POE) for refrigeration systems.

The present invention also includes within its scope a kit in unit dosage form for detecting alkylbenzene or mineral oil impurities in lubricants.

Broadly speaking, the method comprises adding a sufficient amount of a mixture of an alcohol-water to a sample of lubricant. An equal volume of the alcohol-water mixture to an equal volume of the sample is preferred. After mixing, the mixture is compared against a blank. If the mixture remains clear, it indicates less than 2% of impurity which is an acceptable level.

On the other hand, if the mixture produces a white color with opaqueness it indicates there is more than 2% impurity and further purging of the system may be warranted.

The blank may be just water. Typically, the alcohol-water reagent is used as the blank.

In a typical embodiment according to the present invention, a solution comprises about 98.6% by volume of an alcohol and 1.4% by volume of water are mixed together by a simple blending procedure. About 2 ml of this solution is added to about 2 ml of the lubricant to be tested. Alternatively, about 2 ml of lubricant can be added to about 2 ml of the methanol-water mixture.

As described above if the resulting mixture remains clear, there is less than 2% impurity whereas the development of opaqueness indicates more than 2% impurity of either alklybenzene or mineral oil.

In an alternate embodiment according to the present invention, the method can be made to be even more sensitive by increasing slightly (e.g from 1.6% v/v to about 2.0% v/v) of water in the mixture. With the slight increase it will detect even lower concentrations of the impurity (e.g between about 0.5% to about 1%).

Among the alcohol useful in the present invention are typically the lower molecular weight alcohol such as methanol, ethanol, propanol, and the like. Methanol is most preferred because it is readily available. The alcohol-water mixture can be packaged in containers having a volume of at least about 2 ml. From about 2 ml to about 5 ml is most preferred.

In a commercial embodiment, about 2 ml, the methanol-water mixture prepared as described above, is packaged into dosage forms such as plastic or glass ampuls. The ampuls are sealed. In use, the engineer breaks off the seal and adds the contents to 2 ml of the sample lubricant and compares the resulting mixture against a blank. Alternatively 2 ml of the sample can be added to the ampul and conducts the test as described above.

Methanol used in the present invention is a well known material and widely available. See MerckIndex, 11$^{th}$ edition, entry 5868.

In order to illustrate the practice of this invention the following example is included.

EXAMPLE

A master solution of the methanol and water was made using the following concentration by volume.
methanol = 98.6% by volume
water = 1.4% by volume
Several known concentrations of Solest.35 (POE) and Zerol. (alkylbenzene) and Solest-35 and Suniso 3GS (mineral oil) were made as shown in Table 2. In our experiments 2 ml of methanol/water mixture was added to 2 ml of each lubricant. It does not make any difference, whether methanol/water mixture is added to the lubricant or the lubricant is added to the methanol/water mixture. After the addition the test tube was agitated, and the results are summarized in Table 2. As is clear from the table, 2% by volume impurity of alkylbenzene or mineral oil in POE gives a color change indication. This color change will be the basis for an operator in the field to decide whether the compressor needs additional flushing or not. It is emphasized once again that this methanol/water system was made to detect up to 2% impurity.

TABLE 2

Change in Color After Addition of 2.0 ml of Methanol/Water (1.4% Water) in the Lubricant

| No. | Lubricant | Impurity | Color |
|-----|-----------|----------|-------|
| 1 | Solest-35 | None | Transparent No Change |
| 2 | Solest-35 | 0.5% Zerol-150 | Transparent No Change |
| 3 | Solest-35 | 2% Zerol-150 | Opaque, White |
| 4 | Solest-35 | 10% Zerol-150 | Opaque, White |
| 5 | Solest-35 | 20% Zerol-150 | Opaque, White |
| 6 | Solest-35 | 0.5% Suniso 3GS | Transparent No Change |
| 7 | Solest-35 | 2.0% Suniso 3GS | Opaque, White |
| 8 | Solest-35 | 20% Suniso 3GS | Opaque, White |

NOTE:
Solest-35 is a POE lubricant.
Zerol-150 and Suniso 3GS are alkylbenzene and naphthenic lubricant respectively.

What is claimed is:

1. A method for detecting low level of at least one alkylbenzene and mineral oil impurity in polyol ester lubricant for compressors which comprises:
    a) adding a sufficient amount of a mixture of alcohol and water to a sample of said lubricant and;
    b) comparing the clarity of the resulting solution against a blank wherein said clarity indicates substantially pure polyol ester lubricant whereas no clarity indicates said at least one alkylbenzene and mineral oil.

2. A method according to claim 1 wherein said alcohol is methanol.

3. A method according to claim 2 wherein said methanol is a methanol-water mixture comprises about 98.6% v/v of methanol and 1.4% v/v of water.

4. A method according to claim 1 wherein about an equal volume of said mixture is added to about an equal volume of said lubricant.

5. A method according to claim 1 wherein about 2 ml of said mixture is added to about 2 ml of said lubricant.

6. A method according to claim 5 wherein said mixture is a methanol-water mixture as defined in claim 3.

* * * * *